(12) United States Patent  
Ziegler et al.

(10) Patent No.: US 8,520,921 B2  
(45) Date of Patent: Aug. 27, 2013

(54) METHOD FOR RECONSTRUCTING A FLUORESCENT IMAGE OF THE INTERIOR OF A TURBID MEDIUM AND DEVICE FOR IMAGING THE INTERIOR OF A TURBID MEDIUM

(75) Inventors: Ronny Ziegler, Hamburg (DE); Andy Ziegler, Kelburn/Wellington (NZ); Tim Nielsen, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 263 days.

(21) Appl. No.: 12/933,887

(22) PCT Filed: Mar. 20, 2009

(86) PCT No.: PCT/IB2009/051179  
§ 371 (c)(1),  
(2), (4) Date: Sep. 22, 2010

(87) PCT Pub. No.: WO2009/118672  
PCT Pub. Date: Oct. 1, 2009

(65) Prior Publication Data  
US 2011/0026851 A1 Feb. 3, 2011

(30) Foreign Application Priority Data  
Mar. 27, 2008 (EP) .................... 08153363

(51) Int. Cl.  
*G06K 9/00* (2006.01)

(52) U.S. Cl.  
USPC ........... 382/128; 382/100; 382/131; 382/132; 600/437; 600/443; 128/922

(58) Field of Classification Search  
USPC ............... 382/128, 274; 600/425, 317, 407; 356/213; 378/44; 250/458.1  
See application file for complete search history.

(56) References Cited

U.S. PATENT DOCUMENTS

| | | | | |
|---|---|---|---|---|
| 5,865,754 A | * | 2/1999 | Sevick-Muraca et al. | .... 600/476 |
| 6,738,658 B2 | * | 5/2004 | Wake et al. | .... 600/431 |

(Continued)

OTHER PUBLICATIONS

A Koenig, Boutet, Fluorescence diffuse optical tomographic (fDOT) system for samll animal studies, 2007, Proceedings of the 29th Annual International conference of the IEEE.*

(Continued)

*Primary Examiner* — Jayesh A Patel  
*Assistant Examiner* — Iman K Kholdebarin

(57) ABSTRACT

A method for reconstructing a fluorescence image of the interior of a turbid medium is provided. The method comprises the step: accommodating a turbid medium (1) to which a fluorescent contrast agent has been administered in a measurement volume (4). The fluorescent contrast agent is capable of emitting light in a first range of wavelengths upon irradiation with light. The method further comprises: performing attenuation measurements at a plurality of different wavelengths ($\lambda i, \ldots, \lambda k$) by subsequently irradiating the turbid medium (1) with light from a plurality of different source positions and detecting light emanating from the turbid medium (1) in a plurality of detection positions for each source position; reconstructing absorption properties ($\mu a(r, \lambda)$) as a function of the position in the interior of the turbid medium (1) for the plurality of different wavelengths from the attenuation measurements; calculating absorption properties as a function of the position in the interior of the turbid medium (1) for wavelengths of the first range of wavelengths; performing a fluorescence measurement by subsequently irradiating the turbid medium (1) with light causing the fluorescent contrast agent to emit light in the first range of wavelengths from the plurality of source positions and detecting the light emanating from the fluorescent contrast agent in the plurality of detection positions for each source position; and reconstructing a fluorescence image of the spatial distribution of the fluorescent contrast agent in the interior of the turbid medium (1) from the fluorescence measurement using the calculated absorption properties.

15 Claims, 1 Drawing Sheet

(56) References Cited

U.S. PATENT DOCUMENTS

| | | | |
|---|---|---|---|
| 7,828,732 B2* | 11/2010 | Wang et al. | 600/437 |
| 8,070,682 B2* | 12/2011 | Zhu | 600/437 |
| 8,160,320 B2* | 4/2012 | Li | 382/128 |
| 2008/0058638 A1* | 3/2008 | Zhu et al. | 600/425 |
| 2008/0180018 A1* | 7/2008 | Minamoto et al. | 313/483 |
| 2009/0234225 A1* | 9/2009 | Martin et al. | 600/431 |
| 2010/0019170 A1* | 1/2010 | Hart et al. | 250/459.1 |
| 2010/0187441 A1* | 7/2010 | Waldbeser et al. | 250/459.1 |
| 2012/0080877 A1* | 4/2012 | Downing | 283/67 |

OTHER PUBLICATIONS

Koenig et al: "Fluorescence Diffuse Optical (fDOT) System for Small Animal Studies"; Proceedings of the 29th Annual International Conference of the IEEE EMBS Cite Internationale, 2007, pp. 2626-2629.

Ntziachristos et al: "Diffuse Optical Tomography of Highly Heterogeneous Media"; IEEE Transactions on Medical Imaging, vol. 20, No. 6, Jun. 2001, pp. 470-478.

Milstein et al: "Fluorescence Optical Diffusion Tomography"; Applied Optics, Jun. 2003, No. 42, No. 16, pp. 3081-3094.

* cited by examiner

METHOD FOR RECONSTRUCTING A FLUORESCENT IMAGE OF THE INTERIOR OF A TURBID MEDIUM AND DEVICE FOR IMAGING THE INTERIOR OF A TURBID MEDIUM

FIELD OF INVENTION

The present invention relates to a method for reconstructing a fluorescence image of the interior of a turbid medium and to a device for imaging the interior of a turbid medium.

BACKGROUND OF THE INVENTION

In the context of the present application, the term turbid medium is to be understood to mean a substance consisting of a material having a high light scattering coefficient, such as for example intralipid solution or biological tissue. Further, light is to be understood to mean electromagnetic radiation, in particular electromagnetic radiation having a wavelength in the range from 180 nm to 1400 nm. The term "optical properties" covers the reduced scattering coefficient $\mu'_s$ and the absorption coefficient $\mu_a$. Furthermore, "matching optical properties" is to be understood as having a similar reduced scattering coefficient $\mu'_s$ and a similar absorption coefficient $\mu_a$.

A method for imaging the interior of turbid media, e.g. for breast cancer screening, which has become popular in recent years is imaging by use of light, in particular using light in the near infrared (NIR). Such methods are implemented in mammography devices and devices for examining other parts of human or animal bodies. A prominent example for such a method for imaging the interior of a turbid medium by means of light is Diffuse Optical Tomography (DOT). For example, such a DOT device for imaging the interior of a turbid medium uses a light source to irradiate the turbid medium and photodetectors for measuring a part of the light transported through the turbid medium, i.e. its intensity. A control unit is provided for controlling the scanning process. A processing unit is provided for reconstructing an image of the interior of the turbid medium on the basis of the measured intensities. Some of the known devices are particularly adapted for examining female breasts. In order to allow the examination of the turbid medium, the device is provided with a receiving portion enclosing a measurement volume and arranged to receive the turbid medium. Light from the light source is coupled into the receiving volume and into the turbid medium. The light is chosen such that it is capable of propagating through the turbid medium. For imaging an interior of a female breast, light in the NIR (near infrared) is typically used. Scattered light emanating from the turbid medium as a result of coupling light into the receiving volume is coupled out of the receiving volume. Light coupled out of the receiving volume is used to reconstruct an image of an interior of the turbid medium. Due to different sizes of the turbid media to be examined, the size of the receiving portion may not perfectly match the size of the turbid medium, i.e. a space remains between the boundary of the receiving volume and the turbid medium. The part of the turbid medium under investigation is surrounded by a scattering medium (coupling medium) filling the space in the receiving volume. The scattering medium is chosen such that the optical parameters of the scattering medium, such as the absorption and scattering coefficients, are similar to the corresponding optical parameters of the turbid medium. The light source subsequently irradiates the turbid medium from different directions and the photodetectors measure a part of the light transmitted through the turbid medium. A plurality of such measurements are performed with the light directed to the turbid medium from different directions and, based on the results of the measurements, i.e. the obtained data set, the processing unit reconstructs the image of the examined turbid medium.

According to one development of this method, attenuation scans for light are performed in which the attenuation of light is detected for a plurality of combinations of source positions and detection positions. In these measurements the intrinsic contrast of the turbid medium is used, i.e. light at different wavelengths is attenuated by different amounts due to the presence of scatterers and chromophores such as oxy-hemoglobin, deoxy-hemoglobin, water, and lipids. From these attenuation scans, absorption images of the turbid medium can be reconstructed as well as images of physiological parameters such as e.g. the hemoglobin concentration. This technology has become known as Diffuse Optical Tomography (DOT).

According to a further development of this method, a fluorescent contrast agent which preferentially accumulates at lesions in the turbid medium under investigation, e.g. cancerous tissue in a female breast, is administered for the measurement. The turbid medium is irradiated with light from a light source, preferably a laser, and the fluorescent light which is emitted by the turbid medium is detected. From this measurement, a volumetric image of the fluorescence emission by the breast is reconstructed, i.e. exogenous contrast is used. Thus, the spatial distribution of the contrast agent in the turbid medium is reconstructed. This method is called Diffuse Optical Fluorescence Tomography.

Devices have been developed which are adapted to perform both attenuation measurements and fluorescence measurements. In such devices, attenuation measurements are performed for a plurality of wavelengths in a certain range of wavelengths. The data obtained in the attenuation measurements allows reconstructing a spatially resolved image of the absorption properties of the turbid medium for the plurality of wavelengths. Thus, it can be reconstructed from the attenuation measurements how the light travels through the turbid medium at these wavelengths. In order to perform fluorescence measurements, the fluorescent contrast agent is explicitly excited and solely the light emitted by the fluorescent contrast agent is measured. This is for example achieved by introducing appropriate filters in the light paths between the measurement volume and a detection unit. However, the light emitted by the fluorescent contrast agent comprises a band of wavelengths located in a range of wavelengths which can differ from the wavelengths probed by the attenuation measurements. Thus, for the relevant wavelengths of the fluorescence measurement, there arises the problem that it is not known how the light interacts with the turbid medium.

In a method known to the applicant, the approximation is used that the interaction of light with the turbid medium is substantially the same for the wavelengths relevant for the attenuation measurements and for the range of wavelengths relevant for the fluorescence measurement. However, this approximation does not hold in general and the quality of this approximation differs depending on e.g. different patients and the constitution of their tissue. As a result, current methods for reconstructing fluorescence images of the interior of turbid media, i.e. for reconstructing an image of the spatial distribution of the fluorescent contrast in the turbid medium, comprise the problem that concentrations of the fluorescent contrast agent at different positions in the turbid medium cannot be determined to a satisfactory degree from the reconstructed image.

SUMMARY OF THE INVENTION

It is an object of the present invention to provide a method for reconstructing a fluorescence image of the interior of a turbid medium and a device for imaging the interior of turbid media with which the concentrations of a fluorescent contrast agent at different positions in the turbid medium can be determined more accurately from the reconstructed image. Further, this shall be achieved fast and efficiently without requiring additional hardware.

This object is attained by a method for reconstructing a fluorescence image of the interior of a turbid medium according to an embodiment. The method comprises the step: accommodating a turbid medium to which a fluorescent contrast agent has been administered in a measurement volume. The fluorescent contrast agent is capable of emitting light in a first range of wavelengths upon irradiation with light. The method further comprises: performing attenuation measurements at a plurality of different wavelengths by subsequently irradiating the turbid medium with light from a plurality of different source positions and detecting light emanating from the turbid medium in a plurality of detection positions for each source position. The method further comprises: reconstructing absorption properties as a function of the position in the interior of the turbid medium for the plurality of different wavelengths from the attenuation measurements; calculating absorption properties as a function of the position in the interior of the turbid medium for wavelengths of the first range of wavelengths; performing a fluorescence measurement by subsequently irradiating the turbid medium with light causing the fluorescent contrast agent to emit light in the first range of wavelengths from the plurality of source positions and detecting the light emanating from the fluorescent contrast agent in the plurality of detection positions for each source position; and reconstructing a fluorescence image of the spatial distribution of the fluorescent contrast agent in the interior of the turbid medium from the fluorescence measurement using the calculated absorption properties. As a result, the interaction of light having a wavelength in the first range of wavelengths with the turbid medium is estimated more correctly and the concentration and spatial distribution of the contrast agent in the turbid medium can be reconstructed with a higher degree of accuracy. Further, the attenuation measurements performed for discrete wavelengths can be used to achieve this higher degree of accuracy such that no additional hardware is required. "Absorption properties as a function of the position" means that absorption properties are determined in dependency on the position in the turbid medium. A functional dependency (in the mathematical sense) does not necessarily have to be established. The calculated absorption properties are used as input information in the step of reconstructing the fluorescence image.

Preferably, in the step of reconstructing absorption properties, absorption coefficients are calculated. In this case, a known wavelength dependency of the absorption coefficients can be used to achieve an advantageous calculation for the wavelengths of the first range of wavelengths.

According to an aspect, the absorption coefficients are calculated by considering the turbid medium as a linear combination of a plurality of substances and determining the local concentrations of the plurality of substances from the attenuation measurements at the plurality of different wavelengths. In this case, the absorption properties with respect to wavelengths in the first range of wavelengths can be calculated with satisfactory accuracy such that the concentration of the fluorescent contrast agent can be visualized more correctly in the reconstructed fluorescence image.

If the absorption properties for wavelengths of the first range of wavelengths are calculated using a known spectral behavior of the plurality of substances, the absorption properties with respect to wavelengths of the first range can be calculated with satisfactory accuracy. As a result, the reconstructed fluorescence image provides reliable information about the concentrations of the fluorescent contrast agent at the different positions. Thus, a fluorescence image can be provided which allows distinction of malignant lesions from other abnormalities.

If the plurality of substances comprises the fluorescent contrast agent, a fluorescence image providing satisfactory information about the concentration of the fluorescent contrast agent can be reconstructed from the fluorescent measurement even if the concentration of the fluorescent contrast agent is high.

Preferably, the reconstructed fluorescence image is fed back as an input to the step of reconstructing absorption properties as a function of the position in the interior of the turbid medium, and the steps of extrapolating the absorption properties and reconstructing a fluorescence image are iteratively repeated. In this case, the concentration of the fluorescent contrast agent can be determined with improved accuracy even if locations with high concentrations occur in the turbid medium.

The object is further attained by a device for imaging the interior of a turbid medium according to an embodiment. The device comprises: a measurement volume adapted for accommodating a turbid medium to which a fluorescent contrast agent has been administered which is capable of emitting light in a first range of wavelengths upon irradiation; a light source unit adapted to subsequently irradiate the measurement volume with light from a plurality of different source positions; the light source unit being capable of selectively emitting light of a plurality of different wavelengths; and a detection unit adapted to detect light emanating from the measurement volume in a plurality of different detection positions. The device further comprises a control and reconstruction unit adapted to control the device to: perform attenuation measurements at a plurality of different wavelengths by subsequently irradiating the measurement volume with light from a plurality of different source positions and detect light emanating from the measurement volume in a plurality of detection positions for each source position; perform a fluorescence measurement by subsequently irradiating the measurement volume with light causing the fluorescent contrast agent to emit light in the first range of wavelengths from the plurality of source positions and detecting the light emanating from the fluorescent contrast agent in the plurality of detection positions for each source position; reconstruct absorption properties as a function of the position in the measurement volume for the plurality of different wavelengths from the attenuation measurements; calculate absorption properties as a function of the position in the measurement volume for wavelengths of the first range of wavelengths; and reconstruct a fluorescence image of the spatial distribution of the fluorescent contrast agent in the measurement volume from the fluorescence measurement using the calculated absorption properties. As a result, the interaction of light having a wavelength in the first range of wavelengths with the turbid medium is estimated more correctly and the concentration and spatial distribution of the contrast agent in the turbid medium can be reconstructed with a higher degree of accuracy. Further, the attenuation measurements performed for several discrete wavelengths can be used to achieve this higher degree of accuracy such that no additional hardware is required.

If a filter is provided in the device introducible in the light path between the measurement volume and the detection unit for the fluorescence measurement, the reconstruction can be achieved with a limited amount of hardware.

Preferably, the device is a medical image acquisition device.

BRIEF DESCRIPTION OF THE DRAWINGS

Further features and advantages of the present invention will arise from the detailed description of embodiments with reference to the enclosed drawings.

DETAILED DESCRIPTION OF EMBODIMENTS

First Embodiment

An embodiment of the present invention will now be described with reference to FIGS. 1 and 2. The device for imaging the interior of a turbid medium according to the embodiment is a device for diffuse optical tomography (DOT). In particular, the device is adapted for examination of female breasts. The overall construction of such a device is known in the art. The device comprises a bed (not shown) on which the person under examination is lying in a prone position. An opening is formed in the bed below which a measurement volume 4 extends. The measurement volume 4 is shown in FIG. 1.

Figure 1:
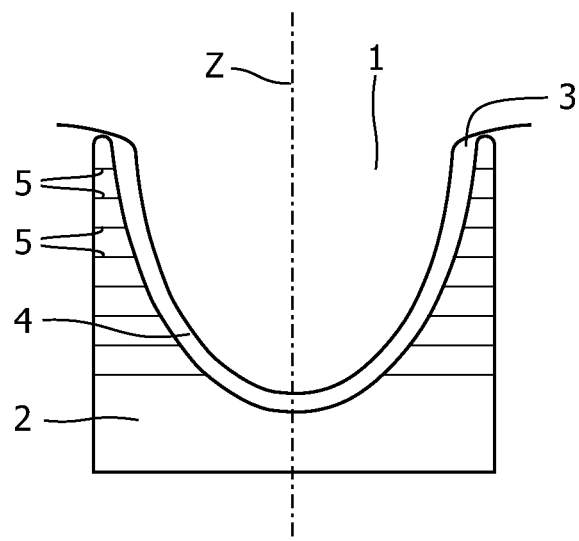
FIG. 1 schematically shows a measurement volume of a device for imaging the interior of a turbid medium.

In the device shown in FIG. 1, the turbid medium 1 to be examined is a female human breast. The measurement volume 4 is bounded by a receiving portion 2 adapted to receive the turbid medium 1, as schematically indicated in FIG. 1. The receiving portion 2 has a cup-like shape and is provided with an opening 3. As can be seen in FIG. 1, the turbid medium 1 to be examined is placed in the measurement volume 4 such that it freely hangs in the measurement volume 4 from the side of the opening 3. The receiving portion 2 serves to position and stabilize the turbid medium 1 which is examined.

Figure 2:
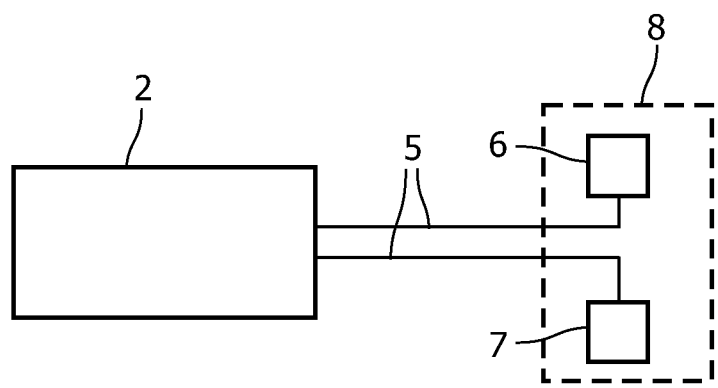
FIG. 2 schematically shows an arrangement of the measurement volume, the light source unit, and the detection unit in the device of FIG. 1.

The inner surface of the receiving portion 2 facing the turbid medium 1 is provided with a plurality of ends of light guides 5 formed by optically guiding fibers connecting to a light source unit 6 and to a detection unit 7, as schematically shown in FIG. 2. The light source unit 6 comprises at least one light source capable of selectively emitting light of a plurality of different wavelengths. Preferably the light source unit 6 comprises a plurality of lasers each emitting monochromatic light but at different wavelengths. In this case, the light source unit 6 is adapted such that light from one of the light sources can be selectively coupled into the measurement volume at a time. The ends of the light guides 5 are distributed on the inner surface of the receiving portion 2. The device is adapted such that light from the light source unit 6 can be directed to the turbid medium 1 from a plurality of different directions (source positions) and light emanating from the turbid medium 1 can be detected by the detection unit 7 in a plurality of different detection positions distributed around the measurement volume 4. In the embodiment, the detection unit 7 is implemented by a plurality of detectors the corresponding light guides 5 of which are distributed on the inner surface of the receiving portion 2. The ends of the light guides 5 at the inner surface of the receiving portion 2 form a plurality of source positions and a plurality of detection positions. In the embodiment the overall number of source positions is equal to the overall number of detection positions; however, the invention is not limited to an equal number. For example, in the device according to the embodiment, 256 different source positions are provided and 256 detection positions, i.e. respective ends of light guides 5 are provided on the inner surface of the receiving portion 2. The light from the light source is subsequently directed to the turbid medium 1 from the 256 source positions and, for each source position, the light emanating from the turbid medium 1 is detected in the 256 detection positions. However, the invention is not limited to these specific numbers.

As schematically shown in FIG. 2, the device comprises a control and processing unit 8 for controlling the acquisition of images and reconstructing images of the interior of the turbid medium 1. The control and processing unit 8 reconstructs an image of the interior of the turbid medium 1 based on the signals from the detection unit 7. For reconstruction, the signals sampled during a scan in which the light is directed to the turbid medium 1 from different directions are used. For reasons of simplicity, these elements of the device for imaging the interior of a turbid medium which are known in the art will not be described again.

The receiving portion 2 is further structured such that a space remains between the inner surface of the receiving portion 2 and the turbid medium 1. For examination, this space is filled with an optically matching medium. The optically matching medium is selected to provide appropriate optical coupling between the turbid medium 1 to be imaged and the source and detection positions distributed on the inner surface. For this purpose, the optically matching medium is provided with optical properties similar to the optical properties of the turbid medium 1 to be examined.

Now, operation of the device according to the embodiment will be described. The device is particularly adapted for a method in which a turbid medium 1 to which a contrast agent has been administered is examined. The contrast agent is a fluorescent contrast agent capable of emitting (fluorescence) light in a first range of wavelengths upon irradiation with suitable light. For example, typical fluorescent dyes used for optical fluorescence tomography emit light in wavelength bands comprising a spectrum from approximately 700-950 nm. The turbid medium 1 to which contrast agent has been administered is placed in the measurement volume 4.

Then, attenuation measurements are performed in which light from the light source unit 6 is subsequently directed to the turbid medium from the plurality of source positions. In the attenuation measurements, attenuation of the light used for irradiating is detected in the plurality of detection positions for each source position as attenuation measurement data, i.e. the attenuation of the incident light is measured. Thus, in the attenuation measurement the intrinsic contrast of the turbid medium 1 is used. The attenuation of the light used for irradiating is measured for a plurality of different wavelengths $\lambda_1, \ldots, \lambda_k$ of the light from the light source unit 6. According to the embodiment, this is accomplished by several different light sources in the light source unit 6, the light sources emitting light at different wavelengths $\lambda_1, \ldots, \lambda_k$. In general, these discrete wavelengths are located in a second range of wavelengths which differs from the first range of wavelengths of the fluorescence spectrum of the fluorescent contrast agent. More specific, in many cases the second range of wavelengths comprises shorter wavelengths. Preferably, the light sources are formed by lasers emitting monochromatic light at different wavelengths such as e.g. 690 nm and 730 nm.

From these attenuation measurements, a three-dimensional image of the absorption properties of the turbid medium 1 can be reconstructed using reconstruction methods known in the art. Since the attenuation measurements are performed for different wavelengths $\lambda_1, \ldots, \lambda_k$, the measurements are sensitive to different constituents of the turbid medium 1. Thus, the concentrations of different constituents of the turbid medium 1 can be reconstructed in a spatially resolved manner. This is done by (mathematically) modeling the turbid medium 1 as a linear combination of a plurality of substances, which has been shown to be a quite good approximation. In other words, the absorption coefficient $\mu_a$ is considered to have the following structure:

$$\mu_a(\lambda, r) = \sum_i c_i \cdot \mu_{ai}(\lambda, r),$$

with $c_i$ being the concentration of constituent i, $\mu_{ai}(\lambda)$ being the (wavelength dependent) molar absorption coefficient of constituent i, r being the position in the turbid medium, and the summation being performed over all considered constituents i. Based on the data from the attenuation measurements, the local combination of the plurality of constituents is reconstructed for each location in the turbid medium 1. This is done making use of the following equation:

$$\frac{\Phi_X}{\Phi_{ref}} \propto \sum_i \varepsilon_i(\lambda_X) \int dr^3 c_i(r) \frac{G_X(s,r)G_X(d,r)}{G_X(s,d)},$$

wherein $\Phi_X$ is the measured intensity at a wavelength $\lambda_X$, $\Phi_{ref}$ is the intensity measured in a reference measurement, i defines the constituents of the turbid medium (such as oxy- and deoxy-hemoglobin, lipid, water, etc.), c is the spectral extinction for each of these constituents, c, is the respective concentration of constituent i, s defines the source position, d defines the detection position, r defines the respective position in the turbid medium, and $G_X$ defines the Green's functions at wavelength $\lambda_X$.

Constituents for which the local concentration can be determined according to this method comprise blood, Hb (oxy-hemoglobin or deoxy-hemoglobin), water, lipid, etc. The wavelengths mentioned above are particularly well suited in this respect. Thus, the absorption properties of the turbid medium 1 in the second range of wavelengths are determined from the attenuation measurements for several discrete wavelengths.

Now, according to the present invention, based on the reconstructed information about the local concentrations of the constituents, the absorption properties of the turbid medium 1 in the first range of wavelengths are extrapolated. This is done in the following way: As has been described above, the local concentrations for several constituents are known from the attenuation measurements. Further, the spectral behavior of these constituents in the first range of wavelengths (which is relevant for the fluorescence measurement described below) is known, e.g. from separate measurements examining such constituents, or the like. Thus, based on the knowledge of the local concentrations of the constituents and of the absorption properties of these constituents in the first range of wavelengths, the absorption properties of the turbid medium 1 in the first range of wavelengths are calculated. In other words, the absorption coefficient $\mu_a(\lambda, r)$ is calculated for the wavelengths $\lambda$ in the first range of wavelengths and for each voxel (volumetric pixel) of the turbid medium. As a consequence, a spatially resolved image of the absorption properties of the turbid medium 1 for the first range of wavelengths is calculated from the attenuation measurements for several discrete wavelengths. Thus, this information is achieved without necessitating additional attenuation measurements in the first range of wavelengths which would require additional hardware and additional measurement time.

Further, according to the embodiment, a fluorescence measurement is performed in which the turbid medium 1 is subsequently irradiated with light from the plurality of source positions. The light used in this fluorescence measurement is chosen such that the fluorescent contrast agent (formed by a fluorescent dye preferentially accumulating in lesions in the turbid medium 1) is stimulated by the light to emit fluorescence light comprising wavelengths in the first range of wavelengths. For each of the plurality of source positions, the fluorescence light emitted by the contrast agent is detected in the plurality of detection positions as fluorescence measurement data. Detection of the fluorescence light is performed by appropriate filtering in the light paths between the measurement volume 4 and the detection unit 7.

Based on the fluorescence measurement data, the control and processing unit 8 reconstructs a volumetric image of the fluorescence emission by the contrast agent distributed in the turbid medium 1. According to the embodiment, for reconstructing the volumetric image of the fluorescence emission, the calculated absorption properties for the first range of wavelengths are used as an input to the reconstruction problem. In other words, the Green's function for the first range of wavelengths is calculated taking into account the calculated absorption properties. According to the embodiment, the reconstruction of the fluorescence image is performed by Born fluorescence reconstruction using a homogenous Green's function incorporating the extrapolated absorption at the first range of wavelengths. The extrapolated absorption may either be incorporated for a typical fluorescence wavelength 4 of the band of fluorescence wavelengths (e.g. a wavelength at which the emittance of the fluorescent contrast agent has its maximum) or for several chosen fluorescence wavelengths to take the complete fluorescence spectrum into account. For example, the following equation is used for calculating the concentration $c_{dye}$ of the fluorescent contrast agent:

$$\frac{\Phi_f}{\Phi_X} \propto \sum_{\lambda_f} \gamma(\lambda_f)\varepsilon_{system}(\lambda_f) \int dr^3 c_{dye}(r) \frac{G_X(s,r)G_f(d,r)}{G_X(s,d)};$$

wherein $\Phi_f$ is the detected intensity of fluorescence light, $\gamma(\lambda_f)$ is the quantum yield (percentage of emitted fluorescence photons per absorbed photons), $\varepsilon_{system}$ is the wavelength dependent detection sensitivity (e.g. determined in a calibration measurement), and $G_f$ is the Green's function at the respective fluorescence wavelength $\lambda_f$, the summation being taken over a plurality of fluorescence wavelengths.

As compared to fluorescence image reconstruction in which the spectral behavior of the absorption in the first range of wavelengths is not taken into account or only estimated to be similar to that for the wavelengths of the attenuation measurements, the reconstructed fluorescence image comprises a higher degree of accuracy with respect to the concentration of the fluorescent contrast agent. Thus, the image quality with respect to information about the concentration of the fluorescent contrast agent at different locations in the turbid medium is improved. As a result, an improved fluorescence image is achieved as compared to former fluorescence reconstructions which do not take factors such as the concentration of chromophores inside the turbid medium (hemoglobin, oxyhemoglobin, water, lipid, etc.) into account.

Second Embodiment

A second embodiment will be described in the following. The second embodiment substantially corresponds to the first embodiment described above and only differs in that the fluorescent contrast agent is considered as one of the constituents the concentration of which is determined from the attenuation measurements in the second range of wavelengths. Thus, according to the second embodiment, the self-absorption of the fluorescent contrast agent for the fluorescence light is taken into account for. This leads to improved fluorescence images, in particular in case of high concentrations of the fluorescent contrast agent.

According to the second embodiment, the concentration $c_f(r)$ of the fluorescent contrast agent and its absorption coefficient $\mu_{af}$ are comprised in the equation $$\mu_a(\lambda, r) = \sum_i c_i(r) \cdot \mu_{ai}(\lambda, r),$$

i.e. the term $c_f(r) \mu_{af}(\lambda, r)$ is taken into account in the summation. Thus, the concentration of the fluorescent contrast agent is already (pre-) calculated from the attenuation measurements. The absorption properties for the first range of wavelengths are then calculated similar to the first embodiment and additionally taking into account the known spectral dependency of the absorption of the fluorescent contrast agent. The Green's function for the respective fluorescence wavelength (or wavelengths) is calculated as described with respect to the first embodiment.

Then, the concentration of the fluorescent contrast agent is calculated from the fluorescence measurement, as in the first embodiment. Thus, according to the second embodiment, the extrapolation of the absorption properties for the first range of wavelengths includes determining a first estimation of the concentration of the fluorescent contrast agent from the attenuation measurements. From the fluorescence measurement, the concentration of the fluorescent contrast agent is calculated again, but now more precisely.

As a consequence, the concentration of the contrast agent is determined with higher accuracy even for high concentrations of the fluorescent contrast agent.

Modification

According to a modification of the second embodiment, all steps are performed as described with respect to the second embodiment. However, after the spatial distribution of the concentration of the fluorescent contrast agent has been reconstructed from the fluorescence measurement, this information is used as an input for the absorption reconstruction again. This means, the concentration of the fluorescent contrast agent determined from the fluorescence measurement is used as $c_f(r)$ in the determination of the concentrations of the plurality of constituents of the turbid medium from the attenuation measurements, and the reconstruction is repeated. These steps are then repeated in a "feedback loop" having a plurality of iterations. For each iteration, an improved reconstruction of the dye concentration is achieved. In an ideal case, the steps described above are repeated until the reconstructed concentration of the fluorescent contrast agent converges to a constant image.

According to this modification, the spatial distribution of the concentration of the fluorescent contrast agent can be determined from the fluorescence measurements with improved accuracy even if high concentrations of the fluorescent contrast agent occur such that a considerable amount of self-absorption of the fluorescent contrast agent occurs.

Although it has been described above with respect to the embodiments that the attenuation measurements are performed before the fluorescence measurement, a skilled person will understand that the order can be reversed.

In the embodiments described above, the detection unit comprises a plurality of different detectors the respective detection positions of which are distributed around the measurement volume. This enables fast and efficient measurements. However, the detection unit may also comprise only one detector the position relative to the measurement volume of which is changed during the measurement in order to detect light in the plurality of different detection positions.

Further, it has been described above that the measurement volume is bounded by a receiving portion having a cup-like shape. However, the measurement volume may also have a different shape, e.g. may be bounded by two parallel plates between which the turbid medium is accommodated in a compressed state during the measurements.

The invention claimed is:

1. A method for reconstructing a fluorescence image of the interior of a turbid medium, the method comprising:
    accommodating a turbid medium to which a fluorescent contrast agent has been administered in a measurement volume, the fluorescent contrast agent being capable of emitting light in a first range of wavelengths upon irradiation with light;
    performing attenuation measurements at a plurality of different wavelengths by subsequently irradiating the turbid medium with light from a plurality of different source positions and detecting light emanating from the turbid medium in a plurality of detection positions for each source position, wherein the plurality of different wavelengths are in a second range of wavelengths that differs from the first range of wavelengths;
    reconstructing absorption properties as a function of the position in the interior of the turbid medium for the plurality of different wavelengths from the attenuation measurements;
    calculating absorption properties as a function of the position in the interior of the turbid medium for the wavelengths of the first range of wavelengths;
    performing a fluorescence measurement by subsequently irradiating the turbid medium with light causing the fluorescent contrast agent to emit light in the first range of wavelengths from the plurality of source positions and detecting the light emanating from the fluorescent contrast agent in the plurality of detection positions for each source position;
    reconstructing a fluorescence image of the spatial distribution of the fluorescent contrast agent in the interior of the turbid medium from the fluorescence measurement using the calculated absorption properties.

2. The method according to claim 1, further comprising, in the step of reconstructing absorption properties, calculating absorption coefficients.

3. The method according to claim 2, wherein the absorption coefficients are calculated by considering the turbid medium as a linear combination of a plurality of substances (i) and determining the local concentrations of the plurality of substances from the attenuation measurements at the plurality of different wavelengths.

4. The method according to claim 3, wherein the absorption properties for wavelengths of the first range of wavelengths are calculated using a known spectral behavior of the plurality of substances.

5. The method according to claim 3, wherein the plurality of substances comprises the fluorescent contrast agent.

6. The method according to claim 5, wherein the reconstructed fluorescence image is fed back as an input to the step of reconstructing absorption properties as a function of the position in the interior of the turbid medium, and the steps of calculating the absorption properties and reconstructing a fluorescence image are iteratively repeated.

7. A device configured to image an interior of a turbid medium, the device comprising:
- a measurement volume adapted for accommodating a turbid medium to which a fluorescent contrast agent has been administered which is capable of emitting light in a first range of wavelengths upon irradiation;
- a light source unit adapted to subsequently irradiate the measurement volume with light from a plurality of different source positions; the light source unit being capable of selectively emitting light of a plurality of different wavelengths;
- a detection unit adapted to detect light emanating from the measurement volume in a plurality of different detection positions; and
- a control and reconstruction unit adapted to:
control the device to perform attenuation measurements at a plurality of different wavelengths by subsequently irradiating the measurement volume with light from the plurality of different source positions and detect light emanating from the measurement volume in a plurality of detection positions for each source position, wherein the plurality of different wavelengths are in a second range of wavelengths that differs from the first range of wavelength;
perform a fluorescence measurement by subsequently irradiating the measurement volume with tight causing the fluorescent contrast agent to emit light in the first range of wavelengths from the plurality of source positions and detecting the light emanating from the fluorescent contrast agent in the plurality of detection positions for each source position;
reconstruct absorption properties as a function of the position in the measurement volume for the plurality of different wavelengths from the attenuation measurements;
calculate absorption properties as a function of the position in the measurement volume for wavelengths of the first range of wavelengths; and
reconstruct a fluorescence image of the spatial distribution of the fluorescent contrast agent in the measurement volume from the fluorescence measurement using the calculated absorption properties.

8. The device according to claim 7, wherein a fitter is provided in the device in a light path between the measurement volume and the detection unit for the fluorescence measurement.

9. The device according to claim 7, wherein the device is a medical image acquisition device.

10. The method according to claim 1, wherein the second range of wavelengths comprises shorter wavelengths than the wavelengths of the first range of wavelengths.

11. The method according to claim 10, wherein the first range of wavelengths is approximately 700 nm to approximately 950 nm, and the second range of wavelengths is approximately 690 nm to approximately 730 nm.

12. The device according to claim 7, wherein the second range of wavelengths comprises shorter wavelengths than the wavelengths of the first range of wavelengths.

13. The device according to claim 12, wherein the first range of wavelengths is approximately 700 nm to approximately 950 nm, and the second range of wavelengths is approximately 690 nm to approximately 730 nm.

14. The device according to claim 7, wherein the light source unit comprises a plurality of discrete light sources each configured to emit light of a corresponding one of the different wavelengths.

15. The device according to claim 14, wherein the light emitting by each of the plurality of discrete light sources is monochromatic.

* * * * *